United States Patent
Meignant

(10) Patent No.: US 6,664,296 B1
(45) Date of Patent: Dec. 16, 2003

(54) UNIT GALENICAL FORMULATION FOR VAGINAL USE AS A LOCAL CONTRACEPTIVE AND/OR TO COMBAT SEXUALLY-TRANSMITTED DISEASES AND/OR HIV

(75) Inventor: Catherine Meignant, Paris (FR)

(73) Assignee: Laboratoire Innothera societe Anonyme, Arcueil (FR)

( * ) Notice: Subject to any disclaimer, the term of this patent is extended or adjusted under 35 U.S.C. 154(b) by 0 days.

(21) Appl. No.: 08/860,222

(22) PCT Filed: Dec. 21, 1995

(86) PCT No.: PCT/FR95/01712

§ 371 (c)(1),
(2), (4) Date: Aug. 19, 1997

(87) PCT Pub. No.: WO96/19195

PCT Pub. Date: Jun. 27, 1996

(30) Foreign Application Priority Data

Dec. 22, 1994 (FR) .............................................. 94 15501

(51) Int. Cl.⁷ .............................................. A61K 31/14
(52) U.S. Cl. ...................................... 514/643; 514/643
(58) Field of Search ......................................... 514/643

(56) References Cited

U.S. PATENT DOCUMENTS 5,466,463 A * 11/1995 Ford ........................... 424/433

FOREIGN PATENT DOCUMENTS

EP  0359402  3/1990
FR  2372635  6/1978

OTHER PUBLICATIONS

Morch Index 10$^{th}$ Ed Abstract #7441,7449,7450,8331, 1985.*

Morton et al. 114CA49596k, 1991.*

Pense et al. 118CA219827P, 1993.*

* cited by examiner

Primary Examiner—Russell Travers
(74) Attorney, Agent, or Firm—Jacobson Holman PLLC

(57) ABSTRACT

This galenical formulation which comprises first an outer envelope including gelatin and secondly a non-aqueous liquid or semi-liquid internal phase containing an active principle in solution is characterized in that the active principle is constituted by a spermicide and in that the internal phase includes, in addition to the active principle: a major proportion of a lipophilic agent compatible with the rubber latex of a condom; in minor proportion at least one hydrodispersible agent; at least one bioadhesion agent; and at least one agent for gelling the lipophilic agent. This galenical formulation for vaginal use provides the known advantages of the soft capsule, having properties that are simultaneously spermicidal, antiseptic, and lubricating, and in addition it is reliably compatible with condoms, without any risk of damaging the rubber latex thereof.

15 Claims, No Drawings

UNIT GALENICAL FORMULATION FOR VAGINAL USE AS A LOCAL CONTRACEPTIVE AND/OR TO COMBAT SEXUALLY-TRANSMITTED DISEASES AND/OR HIV

This application is a 371 of PCT/FR95/07112 filed Dec. 21, 1995 which claims priority from french patent application No. 15501 filed Dec. 22, 1994.

The present invention relates to a unit galenical formulation of the soft capsule type, i.e. comprising firstly an outer envelope comprising gelatin and secondly a non-aqueous liquid or semi-liquid internal phase containing a spermicidal active principle in solution.

More particularly, the invention relates to a galenical formulation of this type for vaginal use as a local contraceptive and/or for combatting sexually-transmitted diseases and/or HIV.

At present, there exist numerous spermicidal substances in the form of vaginal suppositories, creams, cream- or solution-impregnated sponges, and tablets for local contraception. All spermicidal agents are naturally surface-active agents.

For example, U.S. Pat. No. 4,983,393 and U.S. Pat. No. 5,069,906 describe a solidified gel composition which dissolves in the presence of vaginal fluids, EP-A-0 587 431 describes a vaginal suppository which dissolves in the vagina, comprising a hydrosoluble lyophilized foam and a spermicide, and U.S. Pat. No. 4,187,286 describes a vaginal suppository comprising a mixture of polyethylene glycol, a spermicide, a thickening agent, a foaming agent, and alginic acid. EP-A-0 359 402 describes a contraceptive vaginal suppository having prolonged effect comprising a spermicide, a polymer gum, a dispersing agent, and as its major excipient, polyoxyethylene glycol (PEG), but that constitutes a homogeneous and solid galenical formulation of composition that could not be adapted to the internal phase of a soft capsule, given the highly hydrophilic nature of PEG which would spontaneously destroy the gelatin outer phase.

The "soft capsule" galenical formulation is well known, having an outer phase which is initially solid and thus easy to handle and put into place, comprising gelatin, in particular constituted by gelatin and glycerin, enclosing a liquid or semi-liquid internal phase containing a therapeutic agent.

For example, FR-A-2 372 635 describes a soft capsule whose internal phase is constituted for the most part by a surface-active agent, and which is thus incompatible with vaginal use for reasons of mucous membrane intolerance; EP-A-0 121 321 describes a soft capsule comprising an active principle which is dissolved or in suspension, and a composition preventing the soft capsule from becoming brittle.

Also, the development of sexually-transmitted diseases (STD) in recent years, and in particular infection by HIV, has led to an ever-increasing use of condoms.

However, it is recommended that use of a condom should be associated with use of an appropriate lubricating agent, i.e. one that does not degrade the mechanical strength properties of the condom and that does not increase its porosity due to the latex being attacked.

For example, EP-A-0 457 127 describes a lubricant based on silicone oil for treating the latex of condoms, EP-A-0 475 664 describes a lubricating composition and use thereof with condoms, and FR-A-2 666 587 describes a lubricant comprising polydimethylsiloxane.

It is also recommended, for greater security, to associate use of a condom with a spermicide (when the condom is used for contraceptive purposes) and/or with an agent that provides protection against sexually-transmitted infections (when the condom is used for protection against STD).

One of the objects of the invention is to propose a galenical formulation which satisfies these various requirements by means of a unit formulation for vaginal use, providing the known advantages of a soft capsule, presenting properties that are simultaneously spermicidal, antiseptic, and lubricating, and which is also reliably compatible with condoms, without any danger of damaging the rubber latex thereof.

According to bibliographic studies, a large number of vaginally-administered formulations (gels, vaginal suppositories, soft capsules, and the like) have the property of spoiling the physical characteristics of the rubber latex of condoms.

A major problem lies in the fact that the rubber latex of condoms loses its properties, and in particular its bursting strength, when it comes into contact with a large number of vaginally-administered formulations.

In addition, the galenical formulation must be well tolerated, stable, and galenically acceptable.

It must satisfy numerous requirements, and in particular:

it must provide bioadhesion to avoid as much as possible the phenomenon of outflow;

it must ensure that the vehicles are compatible with the active principle;

it must favor uniform mixing of the internal phase with vaginal secretions by being hydrophilic to some extent, while ensuring that its hydrophilic nature is compatible with the outer phase including the gelatin so as to avoid denaturing it (otherwise the capsule would melt on its own before being used); and the ingredients selected must be compatible both with the outer phase and with the rubber latex of condoms.

The present invention solves all of the above-mentioned problems by proposing a unit galenical formulation of the above-specified type, characterized in that the active principle is constituted by a spermicide and in that the internal phase includes, in addition to the active principle: a major proportion of a lipophilic agent compatible with the rubber latex of a condom; a minor proportion of at least one hydrodispersible agent; at least one bioadhesion agent; and at least one agent for gelling the lipophilic agent.

According to various advantageous subsidiary characteristics:

the spermicide is selected from benzalkonium chloride, benzethonium chloride, cetyl pyridinium chloride, methylbenzethonium chloride, tetradecyltri-methyl ammonium bromide, benzalkonium bromide, monylphenyl ethers, lauryl ethers, and octoxynols, the spermicide is more particularly of cationic form, and advantageously benzalkonium chloride;

the lipophilic agent compatible with the rubber latex of a condom is a silicone oil;

the hydrodispersible agent is a non-ionic non-surface-active compound, preferably selected from the group comprising: esters of fatty acids and of polyols; lauric alcohol and polyethylene glycol ether; polyoxyethylene castor oil; polyoxyethylene glycerides; polyoxy-ethylene glycols; sucroglycerides of palm oils; and rectified ethyldiethyleneglycol; and advantageously a mixture of polyoxyethylene glycol and of 7-glyceryl-cocoate of polyoxyethylene glycol;

the bioadhesion agent is a biocompatible polymer, preferably selected from: carboxyvinyl acids; carboxymethylcellulose; sodium carboxymethylcellulose; methyl-cellulose; hydroxypropylcellulose; hydroxypropylmethyl-cellulose; agar-agar; aluminum silicate; carrageenates; and carob gum; and more particularly hydroxypropyl-cellulose;

the agent for gelling the lipophilic agent is selected from the group comprising: silica; aluminum monostearate; aluminum tristearate; and cetyl alcohol; and more particularly silica; and its internal phase compatible with the rubber latex of a condom satisfies the general formula: benzalkonium chloride, 50% solution—0.265 g to 2.65 g; silica—5 g to 7 g; hydroxypropylcellulose—6 g to 8 g; 7-glyceryl-cocoate of polyoxyethylene glycol—9 g to 11 g; polyoxyethylene glycol 400 —4 g to 6 g; silicone oil—q.s. 100 g.

The invention also provides a method of obtaining a unit galenical formulation, the method being characterized in that it consists: a) in adding a solution of benzalkonium chloride to silicone oil while stirring; b) in incorporating polyoxyethylene glycol 400 and 7-glyceryl-cocoate of polyoxyethylene glycol in liquid form to the mixture a); c) in mixing the product b) for sufficient time to obtain good homogenization; d) in adding hydroxypropylcellulose to the product c); e) in mixing the product d); f) in incorporating the silica; and g) in stirring until the final product is obtained which is inserted into the envelope comprising gelatin.

Various advantages and characteristics of the present invention appear from the examples below.

In all of the examples of the present invention, mention is made of the content of the internal phase, it being understood that this phase is inserted into an outer envelope including gelatin, in particular an outer envelope of gelatin/glycerin known as a "soft capsule".

Unless stated to the contrary, the examples are given for a quantity of 100 grams.

EXAMPLE 1

| Benzalkonium chloride, 50% solution | 2.65 g |
|---|---|
| Aluminum tristearate | 2 g |
| Methycellulose | 10 g |
| polyoxyethylene glycerides (Labrafil CS 1944 ®) | 10 g |
| Silicone oil | q.s. 100 g |
| (i.e. 75.35% oil and 10% hydrodispersible agent) | |

EXAMPLE 2

| Nonoxynol 9 | 8 g |
|---|---|
| Cetyl alcohol | 5 g |
| Carboxynvinyl acid (Carbopol 944 P ®) | 2 g |
| Hydroxypropylmethylcellulose | 5 g |
| Polyoxyethylene glycol 400 | 7 g |
| Silicone oil | q.s. 100 g |
| (i.e. 73% oil and 7% hydrodispersible agent) | |

EXAMPLE 3

| Lauryl ether (Laureth 9) | 7 g |
|---|---|
| Silica | 5 g |
| Carboxyvinyl acid (Carbopol 944 P ®) | 2 g |
| Monolaurate of polyoxyethylene glycol 400 | 4 g |
| Polyoxyethylene glycerides (Labrafil CS 1944 ®) | 8 g |
| Silicone oil | q.s. 100 g |
| (i.e. 74% oil and 12% hydrodispersible agent) | |

EXAMPLE 4

| Benzalkonium chloride, 50% solution | 2 g |
|---|---|
| Silica | 5 g |
| Methylcellulose | 8 g |
| Polyoxyethylene castor oil | 5 g |
| 7-glyceryl-cocoate of polyoxyethylene glycol (Cetiol HE ®) | 8 g |
| Silicone oil | q.s. 100 g |
| (i.e. 72% oil and 13% hydrodispersible agent) | |

EXAMPLE 5

| Benzethonium chloride | 1 g |
|---|---|
| Aluminum monostearate | 2 g |
| Hydroxyproplymethylcellulose | 7 g |
| 7-glyceryl-cocoate of polyoxyethylene glycol (Cetiol HE ®) | 9 g |
| Polyoxyethylene glycol 400 | 6 g |
| Silicone oil | q.s. 100 g |
| (i.e. 75% oil and 15% hydrodispersible agent) | |

EXAMPLE 6

| Octoxinol 9 | 6 g |
|---|---|
| Cetyl alcohol | 5 g |
| Carboxyvinyl acid (Carbopol EX 55 ®) | 3 g |
| Polyoxyethylene glycerides (Labrafil CS 1944 ®) | 7 g |
| Silicone oil | q.s. 100 g |
| (i.e. 79% oil and 7% hydrodispersible agent) | |

EXAMPLE 7

| Methylbenzethonium chloride | 1.5 g |
|---|---|
| Silica | 6 g |
| Carboxymethylcellulose | 7 g |
| Monolaurate of polyoxyethylene glycol 400 | 4 g |
| Rectified ethyldiethyleneglycol (Transcutol ®) | 2 g |
| Silicone oil | q.s. 100 g |
| (i.e. 79.5% oil and 6% hydrodispersible agent) | |

EXAMPLE 8

| Benzalkonium chloride, 50% solution | 2.52 g |
|---|---|
| Aluminum tristearate | 1.5 g |
| Methylcellulose | 5 g |

-continued

| | |
|---|---|
| Polyoxyethylene glycerides (Labrafil CS 1944 ®) | 8 g |
| Polyoxyethylene glycol 200 | 4 g |
| Silicone oil | q.s. 100 g |
| (i.e. 78.98% oil and 12% hydrodispersible agent) | |

EXAMPLE 9

| | |
|---|---|
| Benzalkonium chloride, 50% solution | 2.52 g |
| Silica | 6 g |
| Hydroxypropylcellulose | 7 g |
| 7-glyceryl-cocoate of polyoxyethylene glycol (Cetiol HE ®) | 10 g |
| Polyoxyethylene glycol 400 | 5 g |
| Silicone oil | q.s. 100 g |
| (i.e. 69.48% oil and 15% hydrodispersible agent) | |

The unit galenical formulation of the invention as illustrated by the above examples presents the advantage of being simultaneously lubricating and spermicidal, while also having properties that are effective against sexually-transmitted diseases and HIV, and while remaining completely compatible with the rubber latex of condoms.

Compatibility tests between the unit galenical formulation of the invention and the rubber latex of condoms have been performed in compliance with the May 1993 standard AFNOR NF S 97-031 have shown that no significant degradation occurs of the properties of condoms, and in particular of their bursting strength.

Tests have been performed at the National Testing Laboratory on samples presented, namely 50 soft capsules corresponding to the formulation of Example 9 above.

The test procedure was as follows: a burst test (measuring burst pressure and volume) as defined in the May 1993 standard NF S 97-031, §5.2 was performed on 20 male condoms of each reference under the following conditions:

male condoms ready for use (lubricated and individually packaged); and male condoms under the same conditions as above, together with 500±30 mg of the above-referenced product applied thereto with a brush for 30 minutes.

The three references of male condoms used for the tests were as follows:

Prophyltex "SN Spécial", smooth surface, batch No. 231 005, thickness 60 μm;

Prophyltex "Stymulève", textured surface, batch No. 341 201, thickness 60 μm; and Manix "Contact", smooth surface, batch No. LD 103 F12, thickness 50 μm.

The results obtained were as follows:

| | Burst volume (dm³) | | Burst pressure (kPa) | |
|---|---|---|---|---|
| Condom reference | not coated | coated | not coated | coated |
| Prophyltex "SN Special" | | | | |
| Mean value | 30.2 | 40.2 | 1.87 | 1.92 |
| Std. dev. | 4.6 | 1.9 | 0.18 | 0.08 |
| Prophyltex "Stymuleve" | | | | |
| Mean value | 37.9 | 32.2 | 1.65 | 1.60 |
| Std. dev. | 5.2 | 8.2 | 0.09 | 0.10 |
| Manix "Contact" | | | | |
| Mean value | 37.9 | 40.4 | 1.56 | 1.46 |
| Std. dev. | 5.2 | 5.1 | 0.08 | 0.12 |

These tests make it possible to conclude that there is no significant change to the burst pressure or volume before and after applying a quantity of the substance of the invention.

To satisfy concepts of bioadhesion of the galenical formulation of the invention and in order to avoid the outflow phenomenon as much as possible, the internal phase in the examples of the present invention contains biocompatible bioadhesive polymers having the property of incorporating a maximum amount of moisture to increase the viscosity of the unit galenical formulation of the invention and thus prolong in situ maintenance of said formulation.

Compatibility of the vehicles with the cationic surface-active agent constituting the active principle was obtained by using non-ionic excipients.

To satisfy the concepts of bioadhesion, non-ionic polymers compatible with the internal phase were included, with said non-ionic polymers preferably being cellulose derivatives.

The phenomenon of outflow by gelification of the non-aqueous internal phase is avoided as much as possible by using an agent that gels the lipophilic agent.

In the invention, at least one of the ingredients of the internal phase favors obtaining a uniform mixture of vaginal secretions with the lipophilic derivative which is the essential ingredient of the fatty phase, by ensuring that the nature of the unit galenical formulation is somewhat hydrophilic. Nevertheless, this hydrophilic nature must remain compatible with the outer phase since otherwise, the outer gelatin structure would be destroyed under the influence of an internal phase that is too hydrophilic.

The lipophilic component of the invention is compatible with the surface-active agent, with the envelope including the gelatin, and above all with the rubber latex of condoms. In the present invention, the lipophilic agent used is a silicone oil, in particular polydimethylsiloxane having the following formula:

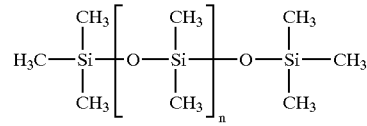

in which n lies in the range 400 to 1200.

This is a clear, colorless, odorless liquid of various viscosities, that is practically insoluble in water and in methanol, that is miscible with ethyl acetate, chloroform, ether, methylethylcetone, carbon tetrachloride, and toluene, and is very poorly soluble in water.

The silicone oil used, which is dimethylpolysiloxane of the Diméticone 1000® type complies with the 10th edition of the French Pharmacopeia and with the 2nd edition of the European Pharmacopeia. Its viscosity lies in the range $950 \times 10^{-6}$ m²/s to $1050 \times 10^{-6}$ m²/s (950 centi-stokes to 1050 centistokes).

The present invention thus relates to a unit galenical formulation for vaginal use in the form of a soft capsule, that is particularly suitable for use with the rubber latex of condoms, which provides contraceptive action with properties that are effective against sexually-transmitted diseases and HIV.

What is claimed is:

1. A unit galenical formulation for vaginal use as a local contraceptive and/or to combat sexually-transmitted diseases and/or HIV, comprising firstly an outer envelope including gelatin and secondly a non-aqueous liquid or semi-liquid internal phase containing an active principle in solution, the formulation being characterized in that the active principle is constituted by a spermicide and in that the internal phase includes, in addition to the active principle: a major proportion of a lipophilic agent compatible with the rubber latex of a condom; a minor proportion of at least one hydrodispersible agent; at least one bioadhesion agent; and at least one agent for gelling the lipophilic agent.

2. A unit galenical formulation according to claim 1, characterized in that the spermicide is selected from benzalkonium chloride, benzethonium chloride, cetyl pyridinium chloride, methylbenzethonium chloride, tetradecyltrimethyl ammonium bromide, benzalkonium bromide, monylphenyl ethers, lauryl ethers, and octoxynols.

3. A unit galenical formulation according to claim 2, characterized in that the spermicide is more particularly of cationic form.

4. A unit galenical formulation according to claim 3, characterized in that the spermicide is benzalkonium chloride.

5. A unit galenical formulation according to claim 1, characterized in that the lipophilic agent compatible with the rubber latex of a condom is a silicone oil.

6. A unit galenical formulation according to claim 1, characterized in that the hydrodispersible agent is a non-ionic non-surface-active compound.

7. A unit galenical formulation according to claim 6, characterized in that the non-ionic, non-surface-active hydrodispersible agent is selected from the group comprising: esters of fatty acids and of polyols; lauric alcohol and polyethylene glycol ether; polyoxyethylene castor oil; polyoxyethylene glycerides; polyoxyethylene glycols; sucroglycerides of palm oils; and rectified ethyldiethyleneglycol.

8. A unit galenical formulation according to claim 7, characterized in that the non-ionic non-surface-active hydrodispersible agent is a mixture of polyoxyethylene glycol and of 7-glyceryl-cocoate of polyoxyethylene glycol.

9. A unit galenical formulation according to claim 1, characterized in that the bioadhesion agent is a biocompatible polymer.

10. A unit galenical formulation according to claim 9, characterized in that the polymer is selected from: carboxyvinyl acids; carboxymethylcellulose; sodium carboxymethylcellulose; methylcellulose; hydroxypropylcellulose; hydroxypropylmethylcellulose; agar-agar; aluminum silicate; carrageenates; and carob gum.

11. A unit galenical formulation according to claim 10, characterized in that the bioadhesion agent is more particularly hydroxypropylcellulose.

12. A unit galenical formulation according to claim 1, characterized in that the agent for gelling the lipophilic agent is selected from the group comprising: silica; aluminum monostearate; aluminum tristearate; and cetyl alcohol.

13. A unit galenical formulation according to claim 12, characterized in that the agent for gelling the lipophilic agent is more particularly silica.

14. A unit galenical formulation according to claim 1, characterized in that its internal phase compatible with the rubber latex of a condom satisfies the general formula:

| | |
|---|---|
| Benzalkonium chloride, 50% solution | 0.265 g to 2.65 g |
| Silica | 5 g to 7 g |
| Hydroxypropylcellulose | 6 g to 8 g |
| 7-glyceryl-cocoate of polyoxyethylene glycol | 9 g to 11 g |
| Polyoxyethylene glycol 400 | 4 g to 6 g |
| Silicone oil | q.s. 100 g |

15. A method of making a unit galenical formulation according to claim 14, characterized in that it consists:

a) in adding a solution of benzalkonium chloride to silicone oil while stirring;

b) in incorporating polyoxyethylene glycol 400 and 7-glyceryl-cocoate of polyoxyethylene glycol in liquid form to the mixture a);

c) in mixing the product b) for sufficient time to obtain good homogenization;

d) in adding hydroxypropylcellulose to the product c);

e) in mixing the product d);

f) in incorporating the silica; and g) in stirring until the final product is obtained which is inserted into the envelope comprising gelatin.

* * * * *